US009481090B2

(12) United States Patent
Sang et al.

(10) Patent No.: US 9,481,090 B2
(45) Date of Patent: Nov. 1, 2016

(54) APPARATUS FOR IDENTIFYING LAYER NUMBER OF AN OBJECT IN A CONTAINER AND SYSTEM FOR AUTOMATICALLY TAKING OUT AN OBJECT

(71) Applicants: BOE TECHNOLOGY GROUP CO., LTD., Beijing (CN); HEFEI BOE OPTOELECTRONICS TECHNOLOGY CO., LTD., Hefei, Anhui (CN)

(72) Inventors: Shengguang Sang, Beijing (CN); Jiangtao Zhang, Beijing (CN); Jun Zhang, Beijing (CN); Jie Deng, Beijing (CN)

(73) Assignees: BOE TECHNOLOGY GROUP CO., LTD., Beijing (CN); HEFFEI BOE OPTOELECTRONICS TECHNOLOGY CO., LTD., Hefei, Anhui (CN)

( * ) Notice: Subject to any disclaimer, the term of this patent is extended or adjusted under 35 U.S.C. 154(b) by 0 days.

(21) Appl. No.: 14/360,873

(22) PCT Filed: Apr. 24, 2013

(86) PCT No.: PCT/CN2013/074624
§ 371 (c)(1),
(2) Date: May 27, 2014

(87) PCT Pub. No.: WO2014/131234
PCT Pub. Date: Sep. 4, 2014

(65) Prior Publication Data
US 2015/0032262 A1    Jan. 29, 2015

(30) Foreign Application Priority Data
Mar. 1, 2013  (CN) .......................... 2013 1 0064919

(51) Int. Cl.
*B25J 9/16* (2006.01)
*B65D 85/48* (2006.01)
(Continued)

(52) U.S. Cl.
CPC ............. *B25J 9/1697* (2013.01); *B25J 9/1687* (2013.01); *B65D 85/48* (2013.01); *G01B 11/14* (2013.01);
(Continued)

(58) Field of Classification Search
CPC ..... B25J 9/1697; B25J 9/1687; G01N 21/84; G01N 21/01; G01N 21/03; G01N 21/0303; G01N 2021/0187; G01N 2201/088; G01B 11/14; B65D 84/48; B65D 85/48; G05B 2219/34204; H01L 21/67265; B65G 2249/02; B65G 49/067; B65G 47/082; G11B 23/113; G02F 1/1303; G02F 2201/58
USPC ...................... 700/258, 259; 901/44, 45, 47; 414/790.1, 937, 940, 932
See application file for complete search history.

(56) References Cited

U.S. PATENT DOCUMENTS 5,999,356 A * 12/1999 Dimitri et al. .................. 360/71
6,188,323 B1 * 2/2001 Rosenquist et al. ....... 340/686.5
(Continued)

FOREIGN PATENT DOCUMENTS

CN         1591775 A      3/2005
CN         2707677 Y      7/2005
(Continued)

OTHER PUBLICATIONS

International Search Report mailed Dec. 12, 2013; PCT/CN2013/074624.
(Continued)

*Primary Examiner* — Jason Holloway
(74) *Attorney, Agent, or Firm* — Ladas & Parry LLP (57) ABSTRACT

An apparatus (01) configured for identifying numbers for layers having objects thereon within a container (02), the objects being accommodated in the container and arranged in layers. the apparatus comprising: an optical fiber sensor (10) configured for detecting presence or absence of the objects from layers within a detecting range; a support frame (20) configured for carrying the optical fiber sensor (10); a guide rail (60) configured for defining a moving direction of the support frame (20); a motor (40) and driving mechanism (30) configured for driving the optical fiber sensor to move along the guide rail; and a controller (50) connected with the optical fiber sensor (10) and the motor (40), wherein the controller (50) is at least configured for obtaining the numbers for the layers having objects thereon according to a moving distance of the support frame (20), in the case that the presence of the objects is detected by the optical fiber sensor (10). In the case of a smaller spacing between the layers in the container (02), the apparatus (01) can accurately obtain the number for the layer in which an object locates, so that a robot arm can take out the object placed at this layer directly. The object is a display panel.

20 Claims, 2 Drawing Sheets

(51) Int. Cl.
*G01B 11/14* (2006.01)
*G01N 21/01* (2006.01)
*G01N 21/84* (2006.01)
*G02F 1/13* (2006.01)

(52) U.S. Cl.
CPC .............. *G01N 21/01* (2013.01); *G01N 21/84* (2013.01); *G02F 1/1303* (2013.01); *G01N 2021/0187* (2013.01); *G01N 2201/088* (2013.01); *G02F 2201/58* (2013.01)

(56) References Cited

U.S. PATENT DOCUMENTS

| | | | | |
|---|---|---|---|---|
| 6,227,373 | B1* | 5/2001 | Stuckey et al. ................ | 209/3.1 |
| 6,822,413 | B2* | 11/2004 | Simondet ............... | B25J 9/1692 318/567 |
| 7,008,884 | B2* | 3/2006 | Wakizako et al. ............ | 438/782 |
| 7,596,456 | B2* | 9/2009 | Mollenkopf et al. ........... | 702/34 |
| 8,435,738 | B2* | 5/2013 | Holmes .......................... | 435/6.1 |
| 8,454,293 | B2* | 6/2013 | Gilchrist et al. .............. | 414/217 |
| 2004/0012363 | A1* | 1/2004 | Simondet ............... | B25J 9/1692 318/568.21 |
| 2004/0075822 | A1* | 4/2004 | Hattori .................. | G03F 7/7075 355/72 |
| 2005/0035313 | A1 | 2/2005 | Garssen et al. | |
| 2005/0036863 | A1* | 2/2005 | Wakizako et al. ............. | 414/448 |
| 2007/0118300 | A1* | 5/2007 | Mollenkopf et al. ........... | 702/33 |
| 2008/0232937 | A1* | 9/2008 | Abe .................. | H01L 21/67265 414/222.02 |
| 2010/0202726 | A1* | 8/2010 | Egalon ................ | G01F 23/2927 385/12 |
| 2015/0030416 | A1* | 1/2015 | Sakiya .............. | H01L 21/67265 414/217.1 |
| 2015/0067929 | A1* | 3/2015 | Blanton ............. | G01B 11/2518 850/1 |

FOREIGN PATENT DOCUMENTS

| | | |
|---|---|---|
| CN | 1815748 A | 8/2005 |
| CN | 101620189 A | 1/2010 |
| CN | 202977420 U | 6/2013 |
| CN | 103217187 A | 7/2013 |
| WO | 0245154 A1 | 6/2002 |

OTHER PUBLICATIONS

Written Opinion of the International Searching Authority dated Nov. 29, 2013; PCT/CN2013/074624.

Written Opinion of the International Searching Authority dated Feb. 14, 2014; PCT/CN2013/087139.

* cited by examiner

APPARATUS FOR IDENTIFYING LAYER NUMBER OF AN OBJECT IN A CONTAINER AND SYSTEM FOR AUTOMATICALLY TAKING OUT AN OBJECT

TECHNICAL FIELD

Embodiments of the present invention relates to an apparatus for identifying layer number for an object in a container and a system for automatically taking out an object.

BACKGROUND

In the manufacture process of a Liquid Crystal display (LCD), firstly, the prepared mother panel needs to be cut so as to obtain panels of desired dimensions, and then, panels of corresponding dimensions (comprising the cell-assembled panels) are placed into a panel box. After that, the robot arm may be used to successively take out panels from the panel box from the bottom up.

The panel box is provided with slots for carrying the panels, by which the panels can be stacked within the panel box layer by layer.

Currently, mapping sensors corresponding to the slots in respective layers are generally used to detect whether there is a panel at the corresponding level, when the vertical spacing between the slots in the panel box is 55 mm. For example, from the bottom up, the slots in the panel box are numbered as a first level, a second level, . . . , and so on, according to the levels at which the slots are located. When the robot arm arrives at the 20th level and it is known that no panel presents at the 20th level through the mapping sensor, the robot arm will directly step over the 20th level and take out panels from the 21th level.

However, in order for a better utilization of space, it is desired to reduce the spacing between the slots in the panel box. For example, the vertical spacing between the slots in the panel box is 10 mm. In such case, the spacing is too small to mount mapping sensors, so that the robot arm detects the presence of a panel from the undermost slot each time, and then performs the action of taking out the panel. Even worse, when no panel presents, the robot arm needs to repeat the taking-out action for 10 times and then notify that no panel is detected, and the robot arm does not perform the action for detecting a panel in the next slot until an operator manually clicks on the button of "detection of next slot". During the process, when there's no panel in a slot at a certain level, the robot arm can not learn whether a panel presents at this level, thus the process of taking out panels, as a whole, is relatively time-consuming.

SUMMARY

The embodiment of the present invention provides an apparatus configured for identifying numbers of layers having objects thereon in a container and a system configured for automatically taking out the objects. The apparatus and the system are capable of accurately learning the numbers for layers where the objects are located in the case that the space between the layers in the container is small. Therefore, robot arm can directly take out the objects placed at these layers and thus corresponding operating time is reduced.

An aspect of the present invention provides an apparatus configured for identifying numbers for layers having objects thereon within a container, the objects being accommodated in the container and arranged in layers, the apparatus comprising: an optical fiber sensor configured for detecting presence or absence of the objects from the layers within a detecting range; a support frame configured for carrying the optical fiber sensor; a guide rail configured for defining a moving direction of the support frame; a motor and driving mechanism configured for driving the optical fiber sensor to move along the guide rail; and a controller connected with the optical fiber sensor and the motor, wherein the controller is at least configured for obtaining the numbers for the layers having objects thereon according to a moving distance of the support frame, in the case that the presence of the objects is detected by the optical fiber sensor.

Another aspect of the present invention provides a system configured for automatically taking out objects accommodated in a container and arranged in layers, layers in the container being arranged from the bottom up in an equidistant way, the system comprises: a robot arm and driving mechanism thereof; and the above mentioned apparatus configured for identifying numbers for layers having objects thereon within the container, the objects being accommodated in the container and arranged in layers, wherein the container comprises a hollow part at a side thereof adjacent to the apparatus, the hollow part is configured for passage of the optical fiber sensor; when the objects are required to be taken out, the controller of the apparatus is configured to firstly determine the number for the layer in the container in which the object closest to the optical fiber sensor is arranged and then control the robot arm to take out the object.

BRIEF DESCRIPTION OF THE DRAWINGS

In the following, a brief introduction of the drawings of the embodiment of present invention will be given so as to describe the technical solutions of the embodiments more clearly, and it is obvious that the drawings described hereinafter just relate to some embodiments of the present invention, and thus are not limitative of the present invention.

REFERENCE NUMERALS

01—an apparatus for identifying numbers of layers having objects thereon within a container, the objects being accommodated in the container and arranged in layers; 02—container; 10—optical fiber sensor; 20—support frame; 201—screw nut; 202—sliding block; 203—first bracket, 204—second bracket; 30—reductor; 40—motor; 50—PLC; 601—ball screw; 602—smooth linear guide rail.

DETAILED DESCRIPTION

To make clearer the object, technical solutions and advantages of the embodiments of present invention, a clear and full description of the technical solution of the embodiment of present invention will be made with reference to the accompanying drawings of the embodiment of present invention. Apparently, the described embodiments are only parts of the embodiments of the present invention, rather than all of the embodiments.

Unless defined otherwise, the technical terms or scientific terminology used herein should take the meaning usually understood by the ordinary skilled in this art. The words "first", "second" as well as similar words used in the description and claims of the present invention do not mean any sequence, quantity or importance, but are only used to distinguish different components. Also, the words "a", "an", "the" and the like do not intent to limit quality, but refer to the existence of at least one. The words "comprise" or "contain" and the like intend to mean that the elements or articles before the words "comprise" or "contain" encompass the elements or articles and the equivalent thereof listed after the words "comprise" or "contain", and do not exclude other elements or articles. The words "upper", "lower", "left", "right" and the like are only used for representing a relative positional relationship; when the described object has changed its absolute position, this relative positional relationship may also vary accordingly.

Figure 1:
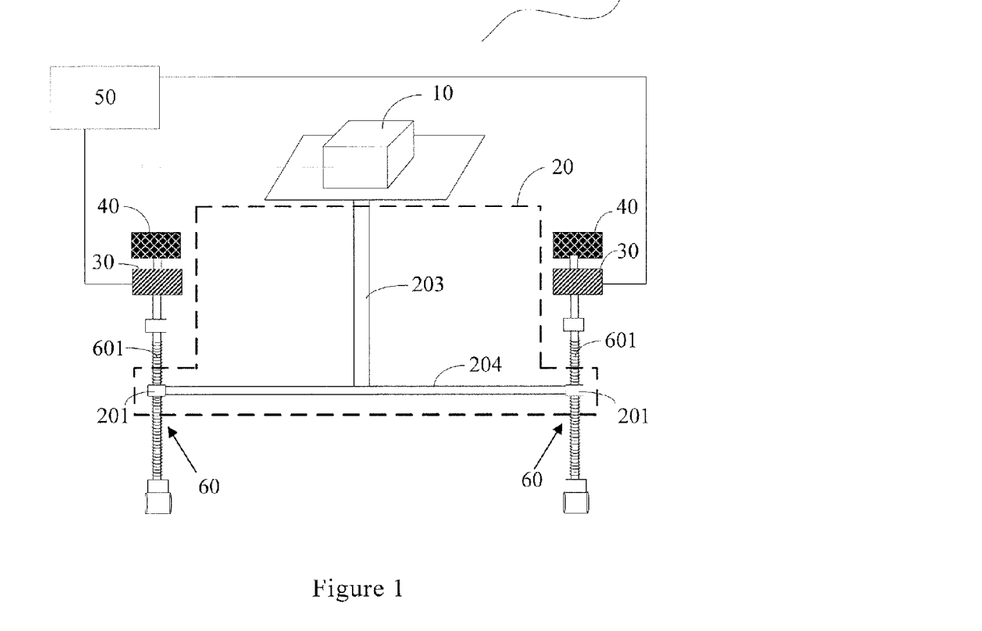
FIG. 1 is a structural schematic view of an apparatus system configured for automatically taking out objects accommodated in a container and arranged in layers for identifying numbers for layers having objects thereon within a container, the objects being accommodated in the container and arranged in layers, according to a first embodiment of the present invention.
Figure 2:
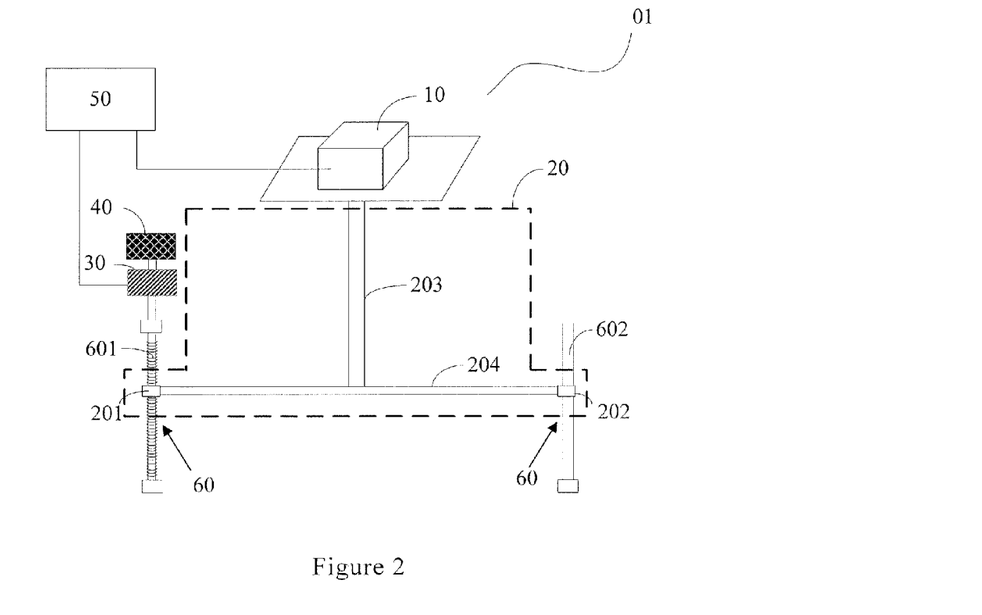
FIG. 2 is a structural schematic view of an apparatus system configured for automatically taking out objects accommodated in a container and arranged in layers for identifying numbers for layers having objects thereon within a container, the objects being accommodated in the container and arranged in layers, according to a second embodiment of the present invention.

The embodiment of present invention provides an apparatus 01 for identifying numbers for layers having objects thereon within a container, the objects being accommodated in the container and arranged in layers, As shown in FIGS. 1 and 2, the apparatus 01 comprises an optical fiber sensor 10, a support frame 20 for carrying the optical fiber sensor, guide rails 60 connected with the support frame 20, a reductor 30 connected with the guide rail 60 and acting as a driving mechanism, a motor 40 connected with the reductor, and a Programmable Logic Controller (PLC) 50 connected with the optical fiber sensor 10 and the motor 40 and acting as a controller.

The optical fiber sensor 10 is used for detecting whether an object presents within the detecting range. The guide rail 60 is used for defining a moving direction of the support frame 20. The motor 40 is used for driving the support frame 20 to move along the guide rail 60. The reductor 30 is used for reducing the rotary speed of the motor 40, so as to reduce the moving speed of the support frame 20. In the case that the presence of an object has been detected by the optical fiber sensor 10, the PLC 50 is used at least for obtaining the number for the layer where the object locates according to the moving distance of the support frame 20.

It should be noted that, firstly, for all the embodiments of the present invention, the term "couple" or "connect" and the like can mean to direct connection or indirect connection. For example, what is meant by "A is connected with B" is that A may be directly connected with B, or that A is directly connected with C and C is directly connected with B, that is, A is indirectly connected with B.

Secondly, the optical fiber sensor 10 can be directly fixed onto the support frame 20; in another case, a carrying platform can be first provided (for example, fixed) on the support frame 20 and then the optical fiber sensor 10 is fixed on the carrying platform. The embodiment of present invention is not limited thereto.

Thirdly, the detection of the presence of an object within the detecting range by the optical fiber sensor 10, for example can be performed by setting the distance from the optical fiber sensor 10 to an object; for example, when the distance from the optical fiber sensor 10 to the object is less than 0.5 mm (detecting distance), the presence of the object in this layer can be determined, and when the distance is greater than 0.5 mm, it is determined that no object presents in this layer. The optical fiber sensor 10 can employ appropriate known optical fiber sensor in this art, description thereof is omitted herein.

Fourthly, for all the embodiments of the present invention, the reductor is illustrated as a driving mechanism by way of example; however, the embodiments of present invention are not limited thereto. Other devices having the same function can also be adopted, no restriction is made here.

Fifthly, for all the embodiments of the present invention, the objects referred to can be any objects arranged layer by layer; the objects can be display panels arranged in layers or similar layered objects which are obtained after cutting process in manufacturing process of LCD, OLED and so on.

Sixthly, in the embodiments of present invention, the layers can be numbered starting from the one closest to the optical fiber sensor 10, that is, from the first layer to the Nth layer (N is an integer). It should be specified that, the layers are numbered with respect to the container, regardless of whether or not an object is placed on such a layer, that is, the number for each layer in the container actually exits, and the object is just laid on a certain layer. For example, in the case that no object is placed in the first layer and an object is placed in the second layer, the number for the layer at which the object is placed is till the second.

In the embodiment of present invention, the controller may not be limited to a PLC. For example, MCU, PC, embedded device, DSP, etc. can also be employed.

The embodiment of present invention provides an apparatus 01 for identifying numbers for layers having objects thereon within a container, the objects being accommodated in the container and arranged in layers. The apparatus 01 comprises an optical fiber sensor 10, a support frame 20 for carrying the optical fiber sensor, guide rails 60 connected with the support frame 20, a reductor 30 connected with the guide rail 60 and acting as a driving mechanism, a motor 40 connected with the reductor, and a PLC 50 connected with the optical fiber sensor and the motor and acting as a controller. The optical fiber sensor 10 is used for detecting the presence or absence of an object from the layer within a detecting range; the guide rail 60 is used for defining a moving direction of the support frame 20; the motor 40 is used for driving the support frame 20 move along the guide rail 60; the reductor 30 is used to reduce the rotary speed of the motor 40; in the case that the optical fiber sensor 10 leant that an object presents, the PLC 50 is used at least for obtaining the number for the layer in which the object locates according to the moving distance of the support frame 20. Therefore, in the case of a smaller spacing between the slots in a panel box, when the downstream robot arm takes out a object for use in a downstream equipment, the number for the layer in which the object locates can be accurately obtained, so that the robot arm can take out the object placed at this layer directly, thus saving operating time for this part.

For example, one example for the guide rail 60 is ball screw 601, in such a case, the support frame 20 can be movably mounted onto the ball screw 601 by means of screw nut 201; alternatively, the guide rail 60 is a smooth linear guide rail 602, in such a case, the support frame 20 is movably mounted onto the smooth linear guide rail 602 by means of slide block 202.

Furthermore, for example, there are two motors 40 and two reductors 30; the two ends of the support frame 20 are connected with the reductors 30 respectively through the ball screws 601. The ball screw 601 has advantages of high positioning accuracy and long performance life and so on.

A first embodiment of present invention provides an apparatus 01 for identifying numbers for layers having display panels thereon within a container, the display panels being accommodated in the container and arranged in layers, in which the display panels is obtained after cutting process and are taken as an example of the objects. As shown in FIG. 1, the apparatus 01 comprises: an optical fiber sensor 10, a support frame 20 for carrying the optical fiber sensor, two ball screws 601 respectively connected to two ends of the support frame 20, two reductors 30 respectively connected with the two ball screws 601, two motors 40 respectively connected with the two reductors 30, and a PLC 50 coupled with the optical fiber sensor 10 and the two motors 40. One end of the support frame 20 is provided with a screw nut 201 matching with the ball screw 601, and the screw nut 201 is mounted onto the ball screw 601; Thus, when the motor 40 is operatively rotating, the reductor 30 connected with the motor 40 can reduce a rotary speed of the motor and make the ball screw 601 rotate, such that the screw nut 201 slide up and down so as to drive the support frame 20 to move.

The reductor 30 is used to reduce the rotary speed of the motor 40, thus the lifting of the support frame 20 is unlikely to be unduly fast, preventing the optical fiber sensor 10 from hitting the display panel. However, if the thread of the ball screw 601 is dense and smooth enough, the reductor 30 can be omitted.

The optical fiber sensor 10 is used to detect the presence or absence of a display panel form a layer within a detecting range. It is possible to specified that the optical fiber sensor 10 detects the presence of an display panel when the optical fiber sensor 10 is about to contact with the display panel, for example, when the distance form the optical fiber sensor 10 to the display panel is less than or equal to 0.5 mm. Here, the PLC 50, which is coupled with the optical fiber sensor 10 and the motors 40, on one hand controls the motors 40 to stop rotation so as to prevent the optical fiber sensor 10 from running into the display panel, and on the other hand obtains the number for the layer in which the object locates.

The PLC 50 may obtain the number for the layer in which the display panel presents through the following computation method:

$$n = \text{roundup}\left(\frac{K \cdot A \cdot B - C}{D}\right) + 1;$$

Wherein, n refers to the number for the layer where the display panel presents, and the value thereof is 1, 2, 3, . . . ; A refers to the number of turns that the motor travels (generally indicated by angular displacement); K refers to a conversion parameter for distance (fixed value); B refers to moving distance (when the motor and the reductor are determined, this value is also a fixed value) of the support frame 20 (in particular, the screw nut 201 connected with the ball screw 601) when the motor rotates a full turn. C refers to vertical distance from the original point of the optical fiber sensor 10 to the first layer in the container for accommodating the display panels (a fixed value); D refers to the spacing between adjacent layers in the container for accommodating the display panels (a fixed value); "roundup" means "adding 1" herein, that is, when the computational result is a number containing a fractional part, then the integral part adds 1.

For example, when the computational result of the $$\frac{K \cdot A \cdot B - C}{D}$$

is 15.1, the value of the $$\text{roundup}\left(\frac{K \cdot A \cdot B - C}{D}\right) \text{ is } \text{``} 15 + 1 = 16\text{''}.$$

Herein, in the container for accommodating the display panels, the layer closest to the optical fiber sensor 10 is numbered as the first layer, regardless of whether or not a display panel is placed on the first layer. The zero point position of the optical fiber sensor 10 is the position of the optical fiber sensor 10 when the apparatus 01 does not get to work.

In the embodiment of present invention, when the PLC 50, which is used as a controller, obtains that the number for the layer where the display panel closest to the optical fiber sensor 10 presents is, for example, the first layer, a downstream robot arm can take out the display panel directly from the first layer for use in a downstream equipment. Then, the PLC 50 controls the motor 40 to work on until the optical fiber sensor 10 detects the next display panel and then the motor 40 stops rotating. For example, when the PLC 50 gets the number for the layer where the next display panel is placed is, for example, the third layer (that is, the second lay has no display panel placed thereon), the downstream robot arm takes out this display panel directly from the third layer without performing related manipulation at the second layer; and then, the above processes are repeated until all the display panels are taken away. Since the apparatus provided by the embodiment of present invention can accurately learn the number for the layer where the display panel is located, the robot arm can directly take out the display panel located at this layer, thus saving operating time for this part.

Furthermore, in the case where a certain layer has display panel placed thereon while the robot arm does not record the information that this layer has a display panel, the apparatus 01 provided by the embodiment of present invention can also prevent the robot arm from colliding with the display panel. In contrast, although the current robot arm would generally record display panels and their corresponding layer numbers, mistakes may occur due to some reasons; in some cases, a certain layer having no object thereon is recorded as having an object, and in other cases, a certain layer having an object thereon is recorded as having no object. In the case that a certain layer having no object thereon is recorded as having an object, the robot arm needs to repeat relevant operations as mentioned in the BACKGROUND section, thus being relatively time-consuming.

It should be noted that although description is made by taking display panel as an example of the object in the embodiment of present invention, the embodiment of present invention is not limited thereto. The apparatus 01 provided by the embodiment of present invention is applicable to identify any objects arranged in layers, and can prevent the downstream robot arm from performing unnecessary related operations when there's no objects in some layers.

For example, there can be one motor 40 and one reductor 30; one end of the support frame 20 is connected with the reductor 30 through the ball screw 601, and the other end thereof is connected with the smooth linear guide rail 602. Related description is provided as follows.

A second embodiment of present invention provides an apparatus 01 for identifying numbers for layers having display panels thereon within a container, the display panels being accommodated in the container and arranged in layers, in which the display panels is obtained after cutting process and are taken as an example of the objects. As shown in FIG. 2, the apparatus 01 comprises: an optical fiber sensor, a support frame 20 for carrying the optical fiber sensor, one ball screw 601 connected with one end of the support frame 20, one reductor 30 connected with the ball screw 601, one motor 40 connected with the reductor 30, a smooth linear guide rail 602 connected with the other end of the support frame 20, and a PLC coupled with the optical fiber sensor 10 and the motor 40. One end of the support frame 20 is provided with a screw nut 201 matching with the ball screw 601, and the screw nut 201 is mounted onto the ball screw 601; The other end of the support frame 20 is provided with a slide block 202 matching with the smooth linear guide rail 602, the slide block 202 is assembled on the smooth linear guide rail 602.

In this way, when the motor 40 is operatively rotated, the reductor 30 connected with the motor 40 can reduce the rotary speed of the motor and make the ball screw 601 rotate, so that the screw nut 201 slides up and down and thus make the end of the support frame 20 provided with the screw nut 201 move. Since the other end of the support frame 20 is connected with the smooth linear guide rail 602 through the slide block 202, when the end of the support frame 20 provided with the screw nut 201 moves, the other end of the support frame 20 connected with the smooth linear guide rail 602 moves correspondingly with the slide block 202, thus making the whole support frame 20 move.

The optical fiber sensor 10 is used to detect the presence or absence of a display panel form a layer within the detecting range. It is possible to specified that the optical fiber sensor 10 detects the presence of an display panel when the optical fiber sensor 10 is about to contact with the display panel, for example, when the distance form the optical fiber sensor 10 to the display panel is less than or equal to 0.5 mm. Here, the PLC 50, which is coupled with the optical fiber sensor 10 and the motors 40, on one hand controls the motors 40 to stop rotation so as to prevent the optical fiber sensor 10 from running into the display panel, and on the other hand obtains the number for the layer in which the object locates.

The computation method for the PLC 50 to get the numbers for the layers in which the display panel is placed can refer to the first embodiment, and repetitive description thereof is omitted here.

The apparatus provided by the present embodiment can not only accurately learn the numbers for the layers in which the object is located, but also save cost since only one motor 40 and one reductor 30 are used.

It should be noted that although description is made by taking display panel as an example of the object in the embodiment of present invention, the embodiment of present invention is not limited thereto. The apparatus 01 provided by the embodiment of present invention is applicable to identify any objects arranged in layers.

For example, referring to FIGS. 1 and 2, the support frame 20 comprises a first bracket 203 and a second bracket 204 orthogonally connected thereto. The first bracket 203 is used for carrying the optical fiber sensor 10.

In this way, when the object to be identified is placed within a relatively small space (for example, a box), only the first bracket 203 carrying the optical fiber sensor 10 is required to enter into, thus extending the application range of the apparatus.

Here, the first bracket 203 is used for carrying the optical fiber sensor 10. For example, it is possible to place and mount a carrying platform onto the topmost end of the first bracket 203.

Further, the position of the first bracket 203 on the second bracket 204 is adjustable.

As such, it is possible to adjust the position of the first bracket 203 according to the position of the object, thus the optical fiber sensor 10 could accurately detect the objects positioned above so that the PLC 50 accurately obtain the number for the layer at which the object presents.

For example, the above mentioned motor 30 is a servomotor capable of converting electrical signal into torque and rotational speed so as to control the driven object. The rotor speed of the servomotor is regulated by an input signal, and can respond quickly. When the servomotor is used as an administering unit in a automatic control system, it has advantageous such as high kinematic accuracy, low fluctuation, smooth and steady operation, short response duration; the servomotor can convert the received electrical signals into angular displacement or angular velocity at the electrode shaft to output, thus the servomotor is widely applied to the apparatus requiring higher accuracy in position or torque, such as the industrial robot arm.

The embodiment of present invention provides an apparatus 01 for identifying numbers for layers having objects thereon within a container, the objects being accommodated in the container and arranged in layers. The apparatus 01 comprises a optical fiber sensor 10, a support frame 20 for carrying the optical fiber sensor, a guide rail connected with the support frame 20, a reductor 30 connected with the guide rail, a motor 40 coupled with the reductor, and a PLC 50 connected with the optical fiber sensor and the motor. The optical fiber sensor 10 is used for detecting the presence or absence of an object form a layer within the detecting range; the guide rail is used for defining the moving direction of the support frame 20; the motor 40 is used for driving the support frame 20 move along the guide rail; the reductor 30 is used to reduce the rotary speed of the motor 40; and the PLC 50 is used at least for, in the case that the optical fiber sensor detect the presence of an object, obtaining the number for the layer in which the object presents according to the moving distance of the support frame 20; As such, in the case of a smaller spacing between the slots in the container, when a downstream robot arm takes out the object for use in a downstream equipment, it is possible to accurately learn the number for the layer in which the object presents, so that the robot arm can directly take out the object placed on this layer, thus saving operating time for this part.

Figure 3:
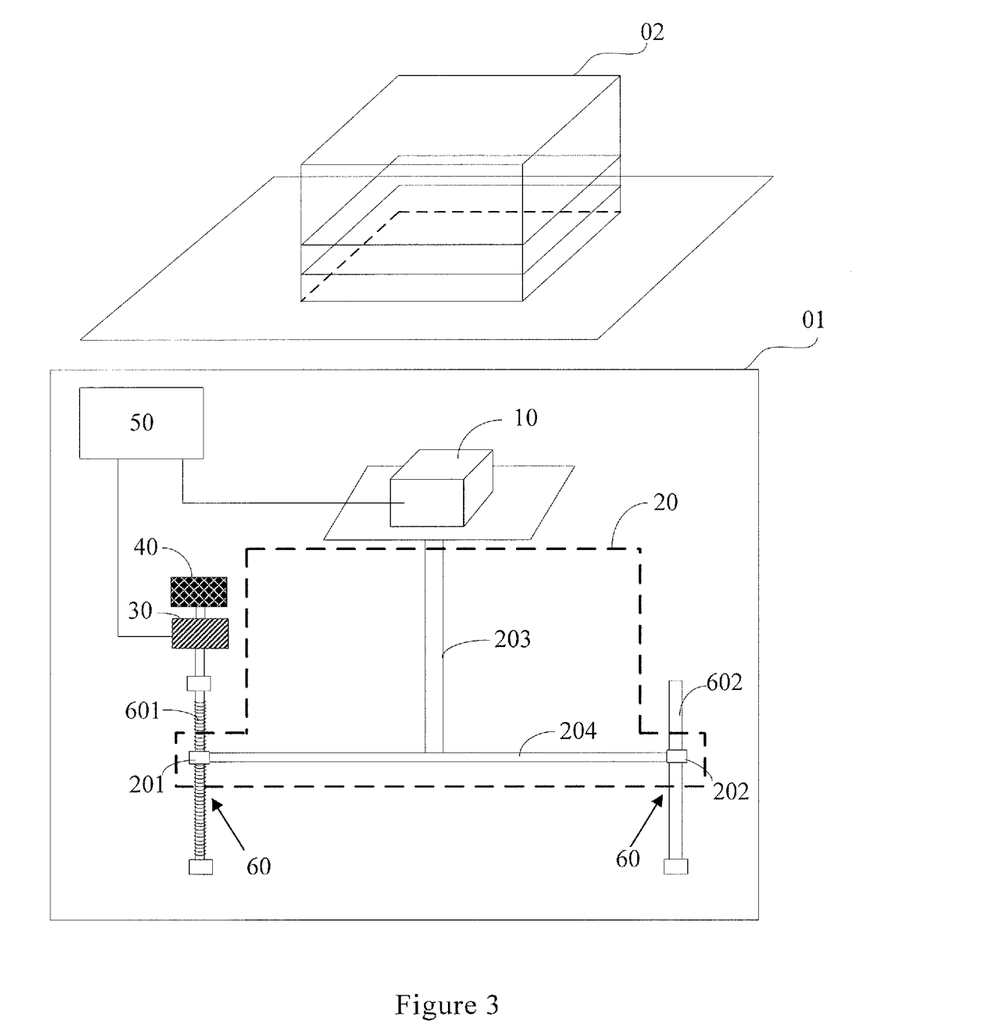
FIG. 3 is a structural schematic view of an system configured for automatically taking out objects accommodated in a container and arranged in layers according to a third embodiment of the present invention.

The embodiment of present invention provides a system for automatically taking out an object from a container accommodating the objects arranged in layers. In the container 02, the objects can be layered in an equidistant way from the bottom up. As shown in FIG. 3, the system comprises a robot arm and its driving mechanism (not shown in the figure), and the above mentioned apparatus 01 for identifying the layer numbers of an objects in a container for accommodating the objects arranged in layers. The optical fiber sensor 10 of the apparatus 01 is provided right below the container 02.

The side of the container 02 close to the apparatus 01 comprises a hollow part (not shown in the figure), the hollow part being used for passage of the optical fiber sensor 10; when it is required to take out an object, the PLC 50 of the apparatus 01, which is used as a controller, firstly determine the number for the layer where the lowermost object is located within the container, and then control the robot arm to take out the lowermost object.

It should be noted that firstly, the phrase "from the bottom up" mentioned herein is described with respect to the optical fiber sensor 10, that is, the position adjacent to optical fiber sensor 10 is the "bottom" position, and the position far away from the optical fiber sensor 10 is the "up" position.

Secondly, for all the embodiments of the present invention, the object referred to can be any objects arranged in layers in the container 02. In particular, the objects can be, for example, display panels arranged in layers or similar layered objects which are obtained after cutting process in manufacturing process of LCD, OLED and so on.

Thirdly, in the embodiments of present invention, the layers can be numbered starting from the one closest to the optical fiber sensor 10, that is, from the first layer to the Nth layer (N is an integer). It should be specified that the layers are numbered with respect to the container, regardless of whether or not an object is placed on such a layer, that is, the number for each layer in the container actually exits, and the object is just laid on a certain layer. For example, in the case that no object is placed in the first layer and an object is placed in the second layer, the number for the layer at which the object is placed is till the second.

As to the container 02, for example, slots for carrying the display panels can be provided on two opposite sides of the container 02, and the slots are arranged in layers from the bottom up in an equidistant manner; when the distance from the optical fiber sensor 10 to the plane defined by two opposite slots are the shortest, the two slots in this plane is the first layer. And, the second layer, the third layer, etc. are successively arranged from the bottom up.

An embodiment of present invention provides a system for automatically taking out objects from a container accommodating the objects arranged in layers, wherein the objects can be arranged from the bottom up in an equidistant way in the container 02; the system comprises a robot arm and its driving mechanism, and the above apparatus 01 for identifying numbers for layers having objects thereon within a container, the objects being accommodated in the container and arranged in layers. The optical fiber sensor 10 of the apparatus 01 is provided right below the container 02; The container 02 comprises a hollow part at a side thereof adjacent to the apparatus 01, the hollow part being used for the passage of the optical fiber sensor 10; in the case that an object is required to be taken out, the PLC 50, which is used as a controller, of the apparatus 01 firstly determines the number for the layer in the container in which the lowermost object is arranged, then controls the robot arm to take out the lowermost object. As such, in the case of a smaller spacing between the slots in the container 02, when a downstream robot arm takes out an object in the container 02 for use in a downstream equipment, it is possible to accurately learn the number for the layer in the container 02 at which the object is placed, so that the robot arm can directly take out the object placed at this layer, thus saving operating time for this part.

For example, the object is display panel.

A third embodiment of present invention provides a system for automatically taking out objects from a container accommodating the objects in layers, as shown in FIG. 3, the objects is display panel after cutting process for example.

The objects in the container 02 may be arranged in layers in an equidistant way from the bottom up. The system comprises: a robot arm and its driving mechanism (not shown in the drawing), and the above apparatus 01 for identifying numbers for layers having objects thereon within the container, the objects being accommodated in the container and arranged in layers.

The optical fiber sensor 10 of the apparatus 01 is located right below the container 02, and the container 02 comprises a hollow part at a side thereof adjacent to the apparatus 01, the hollow part being used for the passage of the optical fiber sensor 10.

The apparatus 01 comprises: an optical fiber sensor, a support frame 20 for carrying the optical fiber sensor, one ball screw 601 connected with one end of the support frame 20, one reductor 30 connected with the ball screw 601, one motor 40 connected with the reductor 30, a smooth linear guide rail 602 connected with the other end of the support frame 20, and a PLC 50 coupled with the optical fiber sensor 10 and the motor 40. One end of the support frame 20 is provided with a screw nut 201 matching with the ball screw 601, and the screw nut 201 is mounted onto the ball screw 601; The other end of the support frame 20 is provided with a slide block 202 matching with the smooth linear guide rail 602, and the slide block 202 is assembled on the smooth linear guide rail 602.

In this way, when the motor 40 is operatively rotated, the reductor 30 connected with the motor 40 can reduce the rotary speed of the motor and make the ball screw 601 rotate, so that the screw nut 201 slides up and down and makes the end of the support frame 20 provided with the screw nut 201 move accordingly. Since the other end of the support frame 20 is connected with the smooth linear guide rail 602 through the slide block 202, when the end of the support frame 20 provided with the screw nut 201 moves, the other end of the support frame 20 connected with the smooth linear guide rail 602 moves correspondingly with the slide block 202, thus causing the whole support frame 20 move.

When the optical fiber sensor 10 detects the presence of a display panel within the detecting range, the PLC 50 coupled with the optical fiber sensor 10 and the motor 40, on the one hand, controls the motor 40 to stop rotating so as to avoid the collision of the optical fiber sensor 10 and the display panel, and on the other hand, obtains the number for the layer in the contain at which the display panel is located and then controls the robot arm to take out the display panel in this layer.

The computation method for the PLC 50 to get the number for the layer in which the display panel is arranged may refer to the first embodiment, repetitive description thereof is omitted here.

Of course, the container 02 can be placed on a carrying platform. The carrying platform also has a hollow region corresponding to the hollow part at the side of the container 02, so as to permitting the passage of the optical fiber sensor 10.

In the embodiment of present invention, display panels are accommodated in the container 02 by slots for carrying display panels. For example, the slots are provided at two opposite sides of the container 02 and arranged in layers from the bottom up in an equidistant way. When it is learned by the PLC 50 that the number for the layer at which the display panel closest to the optical fiber sensor 10 is for example, the first layer, the downstream robot arm can take out this display panel directly from the first layer for use in the downstream equipment. Then, under the control of the PLC 50, the motor 40 keeps on working until a next display panel is detected by the optical fiber sensor 10. When it is learned by the PLC 50 that the number for the layer at which the display panel closest to the optical fiber sensor 10 is for example the third layer (that is, the second has no display panel placed thereon), the downstream robot arm takes out this display panel directly from the third layer without performing related manipulation at the second layer; and then, the above processes are repeated until all the display panels are taken out. Since the apparatus provided by the embodiments of present invention can accurately learn the number for the layer where the display panel is located, the robot arm can directly take out the display panel arranged at this layer, thus saving operating time for this part.

Furthermore, the system for automatically taking out objects from a container accommodating the objects arranged in layers according to the embodiment of present invention can also prevent the collision of the robot arm and the display panel when a certain layer actually has display panel therein while the robot arm does not record the information that this layer has a display panel. In contrast, although the current robot arm would generally record display panels and their corresponding layer numbers, mistakes may occur due to some reasons; in some cases, a certain layer having no object thereon is recorded as having an object, and in other cases, a certain layer having an object thereon is recorded as having no object. In the case that a certain layer having no object thereon is recorded as having an object, the robot arm needs to repeat relevant operations as mentioned in the BACKGROUND section, thus being relatively time-consuming.

The above embodiments are only exemplary embodiments of the present invention, thus are not limitative of the protective scope of the present invention. The protective scope of the present invention is defined by the accompanying claims.

The invention claimed is:

1. An apparatus configured for identifying numbers for layers having objects thereon within a container, the objects being accommodated in the container and arranged in layers to form an object stack, the apparatus comprising:
   an optical fiber sensor configured for detecting presence or absence of the objects from the layers within a detecting range, wherein the optical fiber sensor is located immediately below a lowermost object remaining in the object stack, and when a vertical distance from the optical fiber sensor to a lower surface of the lowermost object remaining in the object stack is less than a detecting distance, the presence of the object is determined by the optical fiber sensor; and when the vertical distance from the optical fiber sensor to the lower surface of the lowermost object remaining in the object stack is more than the detecting distance, the absence of the object is determined by the optical fiber sensor;
   a support frame configured for carrying the optical fiber sensor;
   a guide rail configured for defining a vertical moving direction of the support frame, wherein the optical fiber sensor is located immediately below the lowermost object remaining in the object stack during moving along the vertical moving direction of the support frame;
   a motor and driving mechanism configured for driving the optical fiber sensor to move along the guide rail; and
   a controller connected with the optical fiber sensor and the motor,
   wherein the controller is at least configured for obtaining the numbers for the layers having objects thereon according to a moving distance of the support frame, in a case that the presence of the objects is detected by the optical fiber sensor.

2. The apparatus according to claim 1, wherein the guide rail is a ball screw, and the support frame is movably mounted onto the ball screw through a screw nut; or
   the guide rail is a smooth linear guide rail, and the support frame is movably mounted onto the smooth linear guide rail through a slide block.

3. The apparatus according to claim 1, wherein the driving mechanism is a reductor connected between the support frame and the motor, and is configured for reducing a traveling speed of the support frame.

4. The apparatus according to claim 3, wherein the apparatus comprises two motors and two reductors;
   both ends of the support frame are connected with the reductors through ball screws respectively.

5. The apparatus according to claim 3, wherein the apparatus comprises one motor and one reductor;
   one end of the support frame is connected with the reductor through ball screw, and the other end is connected with the smooth linear guide rail.

6. The apparatus according to claim 1, wherein the support frame comprises a first bracket and a second bracket orthogonally connected with each other, and the first bracket is configured for carrying the optical fiber sensor.

7. The apparatus according to claim 6, wherein the position of the first bracket on the second bracket is adjustable.

8. The apparatus according to claim 1, wherein the motor is a servomotor.

9. A system configured for automatically taking out objects accommodated in a container and arranged in layers, layers in the container being arranged from the bottom up in an equidistant way, the system comprises:
   a robot arm and driving mechanism thereof; and
   an apparatus configured for identifying numbers for layers having objects thereon within the container, the objects being accommodated in the container and arranged in layers to form an object stack, the apparatus comprising:
   an optical fiber sensor configured for detecting presence or absence of the objects from the layers within a detecting range, wherein the optical fiber sensor is located immediately below a lowermost object remaining in the object stack, and when a vertical distance from the optical fiber sensor to a lower surface of the lowermost object remaining in the object stack is less than a detecting distance, the presence of the object is determined by the optical fiber sensor; and when the vertical distance from the optical fiber sensor to the lower surface of the lowermost object remaining in the object stack is more than the detecting distance, the absence of the object is determined by the optical fiber sensor;
   a support frame configured for carrying the optical fiber sensor;
   a guide rail configured for defining a vertical moving direction of the support frame, wherein the optical fiber sensor is located immediately below the lowermost object remaining in the object stack during moving along the vertical moving direction of the support frame;

a motor and driving mechanism configured for driving the optical fiber sensor to move along the guide rail; and a controller connected with the optical fiber sensor and the motor, wherein the controller is at least configured for obtaining the numbers for the layers having objects thereon according to a moving distance of the support frame, in a case that the presence of the objects is detected by the optical fiber sensor, wherein the container comprises a hollow part at a side thereof adjacent to the apparatus, the hollow part is configured for passage of the optical fiber sensor.

10. The system according to claim 9, wherein the objects are display panels.

11. The apparatus according to claim 2, wherein the driving mechanism is a reductor connected between the support frame and the motor, and is configured for reducing a traveling speed of the support frame.

12. The apparatus according to claim 11, wherein the apparatus comprises two motors and two reductors; both ends of the support frame are connected with the reductors through ball screws respectively.

13. The apparatus according to claim 11, wherein the apparatus comprises one motor and one reductor; one end of the support frame is connected with the reductor through ball screw, and the other end is connected with the smooth linear guide rail.

14. The apparatus according to claim 2, wherein the support frame comprises a first bracket and a second bracket orthogonally connected with each other, and the first bracket is configured for carrying the optical fiber sensor.

15. The apparatus according to claim 3, wherein the support frame comprises a first bracket and a second bracket orthogonally connected with each other, and the first bracket is configured for carrying the optical fiber sensor.

16. The apparatus according to claim 4, wherein the support frame comprises a first bracket and a second bracket orthogonally connected with each other, and the first bracket is configured for carrying the optical fiber sensor.

17. The apparatus according to claim 5, wherein the support frame comprises a first bracket and a second bracket orthogonally connected with each other, and the first bracket is configured for carrying the optical fiber sensor.

18. The apparatus according to claim 14, wherein the position of the first bracket on the second bracket is adjustable.

19. The apparatus according to claim 15, wherein the position of the first bracket on the second bracket is adjustable.

20. The system according to claim 9, the controller of the apparatus is configured to determine the number for the layer in the container in which the object closest to the optical fiber sensor is arranged and control the robot arm to take out the object, in response to that the objects are required to be taken out.

* * * * *